United States Patent
Nuccio

[19]

[11] Patent Number: 5,954,951
[45] Date of Patent: Sep. 21, 1999

[54] DEVICE FOR COLLECTING A SAMPLE OF USED DIALYSIS FLUID

[75] Inventor: Antonino Nuccio, Reggio Emilia, Italy

[73] Assignee: Hospal AG, Basel, Switzerland

[21] Appl. No.: 08/849,394

[22] PCT Filed: Oct. 10, 1996

[86] PCT No.: PCT/IB96/01071

§ 371 Date: Aug. 5, 1997

§ 102(e) Date: Aug. 5, 1997

[87] PCT Pub. No.: WO97/13535

PCT Pub. Date: Apr. 17, 1997

[30]   Foreign Application Priority Data

Oct. 12, 1995 [FR] France .................................. 95 12187

[51] Int. Cl.⁶ ............................ B01D 17/12; B01D 61/34
[52] U.S. Cl. ........................ 210/87; 73/863.02; 210/93; 210/101; 210/257.2; 210/929
[58] Field of Search ..................... 73/861.01, 861.02, 73/863.02; 210/87, 93, 96.2, 101, 321.65, 257.2, 646, 739, 929, 103; 604/4.6; 436/480

[56]   References Cited

U.S. PATENT DOCUMENTS

| | | |
|---|---|---|
| 4,244,787 | 1/1981 | Klein et al. . |
| 4,508,622 | 4/1985 | Polaschegg et al. .................. 210/96.2 |
| 5,442,969 | 8/1995 | Troutner et al. ..................... 73/863.02 |
| 5,518,623 | 5/1996 | Keshaviah et al. .................... 210/96.2 |
| 5,567,320 | 10/1996 | Goux et al. ............................ 210/96.2 |
| 5,725,773 | 3/1998 | Polaschegg ............................. 210/646 |
| 5,744,031 | 4/1998 | Bene .................................... 210/96.2 |
| 5,788,846 | 8/1998 | Sternby .................................. 210/646 |

FOREIGN PATENT DOCUMENTS

| | | |
|---|---|---|
| 0 621 046 A1 | 10/1994 | European Pat. Off. . |
| 0 711 569A1 | 5/1996 | European Pat. Off. . |
| 2 696 644A1 | 4/1994 | France . |
| WO 82/04127 | 11/1982 | WIPO . |

*Primary Examiner*—Joseph W. Drodge
*Attorney, Agent, or Firm*—Finnegan, Henderson, Farabow, Garrett & Dunner, L.L.P.

[57] ABSTRACT

A sampling system for a blood treatment circuit is disclosed, and is designed to collect a sample representative of all waste liquid discharged from a blood treatment apparatus during a treatment session. The circuit includes a feed line for supplying fresh treatment liquid to the blood treatment apparatus and a discharge line for evacuating waste liquid. A withdrawal line connects the discharge line to a collecting container, and a flow meter in each of the discharge line and the withdrawal line measures liquid flow. A controllable flow restrictor such as a valve is provided in the withdrawal line. A controller selectively opens the flow restrictor each time a predetermine volume is measured in the discharge line and closes the flow restrictor each time another predetermined volume is measured in the withdrawal line.

20 Claims, 2 Drawing Sheets

5,954,951

DEVICE FOR COLLECTING A SAMPLE OF USED DIALYSIS FLUID

This application is a 371 of international application PCT/IB96/01071, filed Oct. 10, 1996.

FIELD OF THE INVENTION

The invention relates to a device for collecting a waste liquid sample representative of all the waste liquid discharged at any time from the beginning of a session for blood treatment by extracorporeal circulation. The invention finds a specific application in the treatment of patients suffering from chronic renal deficiency who are subjected, generally three times weekly, to a haemodialysis, haemofiltration or haemodiafiltration session.

DESCRIPTION OF THE RELATED ART

For the record, haemodialysis consists in circulating, on either side of the semi-permeable membrane of a haemodialyser, the blood of a patient and a treatment liquid which is substantially isotonic with the blood, so that, during the diffusive transfer which is established across the membrane for the substances having different concentrations on either side of the membrane, the blood impurities (urea, creatinine, and the like) migrate from the blood towards the treatment liquid. The electrolytic concentration of the treatment liquid is also generally chosen to correct the electrolytic concentration of the blood of the patient.

Haemofiltration consists in extracting from the blood, by ultrafiltration through the semi-permeable membrane of an exchanger, a predetermined volume of plasma water laden with impurities (filtrate). This convective transfer is caused by a pressure difference created on either side of the membrane of the exchanger. The filtrate is compensated for in part by a substitution liquid infused into the patient.

Haemodiafiltration is a combination of the two treatments, the principles of which have just been restated.

In order to evaluate the effectiveness of a treatment session of this type, that is to say in order also to verify the appropriateness of the prescription (electrolytic composition of the treatment liquid, ultrafiltration flow rate, duration of the session, and the like) to the specific requirements of each patient, it is of the greatest advantage to be able to measure the amount of impurities extracted from the blood during the treatment session. In particular, knowledge of the amount of urea removed during a session makes it possible to calculate the purifying efficiency of the exchanger used (true clearance K for urea) and the dialysis dose administered KT/V by solving the equation $$C_{UR(aft)} = C_{UR(bef)} \times e^{-KT/V}$$

in which $C_{UR(aft)}$ is the concentration of urea in the blood after treatment, $C_{UR(bef)}$ is the concentration of urea in the blood before treatment, K is the true clearance for urea, T is the duration of the treatment and V is the total volume of water of the patient (Gotch F. A., Sargent S. A., A mechanistic analysis of the National Cooperative Dialysis Study (NCDS). Kidney Int., 1985, 28, 526–34).

Measuring the amount of impurities removed during a treatment session, in particular the amount of urea, poses a practical problem on account of the volume of waste liquid which is produced, approximately one hundred and twenty liters during a haemodialysis session. The storage of such a volume of liquid, for the purpose of analyzing its contents on completion of the treatment session, is in fact ruled out, in particular for health reasons.

Document EP 0,621,046 describes a device which makes it possible to solve this problem. According to this document, a device for collecting a waste liquid sample representative of all the waste liquid discharged during the treatment session comprises:
- a waste liquid withdrawal line having a first end connected to a waste liquid discharge line of an apparatus for treatment of blood by extracorporeal circulation and a second end which can be connected to a collecting container;
- a flowmeter arranged on the waste liquid discharge line upstream of the connection of the withdrawal line to the discharge line; and
- a pump for causing a metered flow of waste liquid into the collecting container as a function of the data supplied by the flowmeter.

It is known that pumps are metering means whose accuracy does not exceed, in particular at low flow rates, 5 to 10% according to the type of pump used. This absence of accuracy naturally has repercussions on the representativeness of the sample collected. Moreover, the method of operation of certain types of apparatuses for extracorporeal treatment of the blood, as well as certain types of treatment, have a further detrimental effect on this representativeness.

SUMMARY OF THE INVENTION

One aim of the invention is to produce a waste liquid sample withdrawal device which is simultaneously accurate, simple and reliable, whatever the type of treatment prescribed and the method of operation of the blood treatment apparatus used.

To achieve this aim, a device to collect a waste liquid sample representative of all the waste liquid discharged at any time from the beginning of a treatment session carried out by means of an apparatus for treatment of blood by haemodialysis and/or haemofiltration, is designed, in accordance with the invention, comprising a feed line for fresh treatment liquid which can be connected to an inlet of a haemodialyser/haemofilter and a main waste liquid discharge line which can be connected to an outlet of a haemodialyser/haemofilter, this device comprising:
- a waste liquid withdrawal line having a first end connected to the main waste liquid discharge line and a second end which can be connected to a collecting container,
- first means for measuring an amount of liquid arranged on the main discharge line upstream of the connection of the withdrawal line to the main discharge line,
- means for causing a metered flow of waste liquid into the collecting container as a function of the data supplied by the first measurement means comprising:
    - second measurement means for measuring an amount of liquid arranged on the withdrawal line,
    - obturation means arranged on the withdrawal line, and
    - control means for controlling, during a treatment by dialysis, the opening of the obturation means each time that the first measurement means have measured a first predetermined amount V of waste liquid and for controlling the closing of the obturation means each time that the second measurement means have measured a second predetermined amount v of waste liquid.

According to one embodiment of the invention, the device is designed to interact with an apparatus for treatment of blood by haemodialysis and/or haemofiltration comprising a secondary waste liquid discharge line connected, upstream of the first measurement means, to the main discharge line, this line being equipped with an extraction pump and with third measurement means for measuring an amount of liquid. The device then additionally comprises a secondary waste liquid withdrawal line having a first end connected to the secondary discharge line, downstream of the third measurement means, and a second end which can be connected to the collecting container. The secondary discharge line is equipped with obturation means and with fourth means for measuring an amount of liquid. The control means are designed in addition to control, during a treatment by haemofiltration, the opening of the means for obturation of the secondary withdrawal line each time that the third measurement means have measured a first predetermined amount V' of waste liquid and to control the closing of these obturation means each time that the fourth measurement means have measured a second predetermined amount v' of waste liquid. The second and fourth measurement means are advantageously coincident and are arranged on a portion of line common to the two withdrawal lines.

By virtue of this arrangement, if the doctor decides, during a dialysis session, to subject the patient, for an appreciable period of time, to a pure haemofiltration sequence, the representativeness of the sample collected is not detrimentally affected.

According to another embodiment of the invention, the device is designed to interact with an apparatus for treatment of blood by haemodialysis and/or haemofiltration comprising means for making possible, during calibration phases, the circulation of fresh treatment liquid in a portion of the main discharge line comprising the first measurement means. The control means are then additionally designed to control, during calibration phases, the closing of the means for obturation of the withdrawal line.

In apparatuses which contain similar measuring instruments (flowmeters, conductivity probes, and the like) arranged in the dialysis liquid circuit upstream and downstream of the exchanger, it is commonplace, for calibration purposes, to bypass the exchanger at regular time intervals, so as to cause fresh dialysis liquid to circulate in the upstream measuring instrument as in the downstream measuring instrument.

By virtue of the embodiment which has just been mentioned, the device does not withdraw fresh treatment liquid during the calibration periods.

According to one characteristic of the invention, the device contains means for adjusting the flow rate in the waste liquid withdrawal line connected to the main discharge line.

Other characteristics and advantages of the invention will become apparent on reading the following description.

Reference will be made to the appended drawings in which:

DESCRIPTION OF THE PREFERRED EMBODIMENTS

Figure 1:
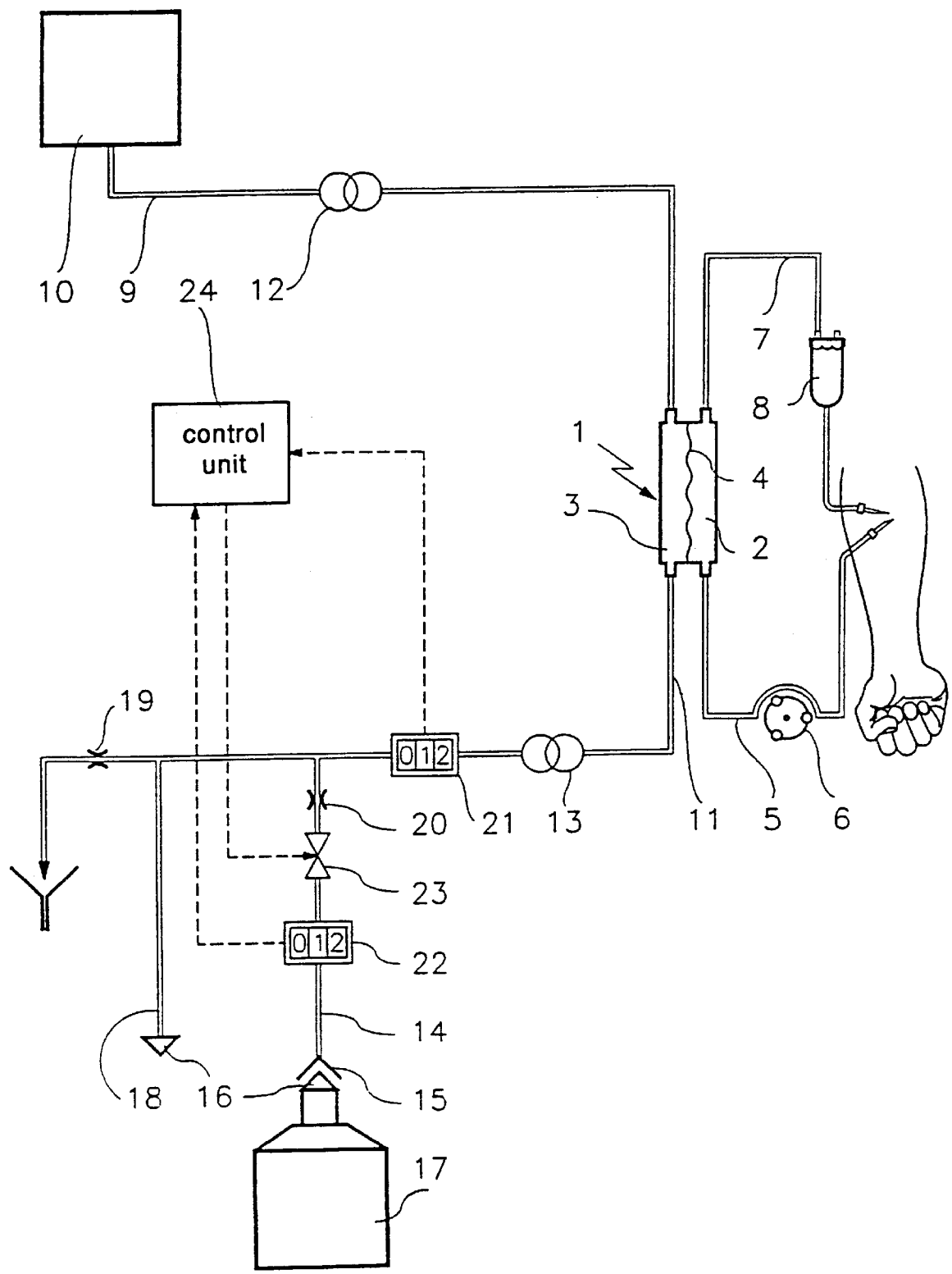
FIG. 1 is a simplified diagram of an apparatus for treatment of blood by extracorporeal circulation in accordance with a first embodiment of the invention.

The blood treatment apparatus presented in FIG. 1 contains an exchanger 1 having a first compartment 2 and a second compartment 3 separated by a semi-permeable membrane 4 and connected respectively to a circuit for extracorporeal blood circulation and to a dialysis liquid circuit.

The circuit for extracorporeal blood circulation comprises a withdrawal line 5 connected to an inlet of the first compartment 2 and a return line 7 connected to an outlet of the first compartment. A circulation pump 6 is arranged on the withdrawal line 5 and a bubble trap 8 is interposed on the return line 7.

The dialysis liquid circuit comprises a feed line 9 for fresh dialysis liquid, having an end connected to a dialysis liquid generator 10 and another end connected to an inlet of the second compartment 3, and a discharge line 11, having an end connected to an outlet of the second compartment 3 and an end connected to the drain.

The dialysis liquid circuit is equipped with two circulation pumps 12, 13 arranged respectively upstream and downstream of the exchanger 1, the flow rates of which are controlled so that the flow rate of the plasma water ultrafiltrating through the membrane 4 is equal to a desired flow rate.

In accordance with the invention, the treatment apparatus which has just been described is equipped with a device for collecting a waste liquid sample representative, at any time, of all the waste liquid discharged since the beginning of the treatment session.

This device comprises a withdrawal line 14 having an end connected to the discharge line 11 and another end equipped with a connector 15 capable of interacting with a complementary connector 16 of a collecting container 17. To enable the withdrawal line 14 to be cleaned and disinfected during maintenance cycles of the treatment apparatus, a looping line 18 is connected to the discharge line 11, the free end of which is equipped with a connector 16 complementary with the connector 15. The discharge line 11 and the withdrawal line 14 are each equipped with a constriction element 19, 20 respectively arranged downstream of their junction. The constriction elements 19, 20 are calibrated so that the ratio of the flow rates of the fluid circulating in the two lines corresponds approximately to a fraction of the total volume of liquid to be sampled (ten per cent, for example) which is also a multiple of the sampling flow rate. The constriction element 19 arranged on the discharge line 11 is preferably composed of an attachment of the treatment apparatus which fulfills another specific function, such as a temperature exchanger. The constriction element 20 arranged on the withdrawal line 14 can be composed of a portion of line having a calibrated diameter.

The sampling device according to the invention additionally comprises first means for measuring an amount of liquid, such as a volumetric meter 21, arranged on the discharge line 11 upstream of its junction with the withdrawal line 14, second means for measuring an amount of liquid, such as a liquid volumetric meter 22, arranged on the withdrawal line 14, and obturation means, such as a valve 23, also arranged on the withdrawal line 14. A control unit 24 receives the signals emitted by the two volumetric meters 21, 22 and controls the opening of the valve 23 according to a sequence such that the volume of liquid collected in the container 17 is equal, at any time, to a predetermined fraction (one per cent, for example) of the total volume of the waste liquid which has flowed in the discharge line 11 since the beginning of the session.

The operation of this device is as follows: after the circuit for extracorporeal blood circulation and the dialysis liquid circuit have been connected to the exchanger 1 and then rinsed and filled, the blood withdrawal line 5 and blood return line 7 are connected to the blood circuit of a patient.

An empty waste liquid sample collecting container 17 is connected to the sample withdrawal line 14 by means of the connectors 15, 16.

The blood circulation pump 6 is then actuated, as well as the pumps 12, 13 of the dialysis circuit, the flow rates of which are adjusted so that the second compartment 3 of the exchanger 1 has a low pressure with respect to the first compartment 2 and so that consequently a predetermined plasma water fraction migrates from the blood circuit towards the dialysis liquid circuit. Purification by convective and diffusive transfer begins in the exchanger.

As soon as the rinsing liquid contained in the waste liquid discharge line 11 has been purged, the sampling device according to the invention is actuated. Each time that the first volumetric meter 21 has measured a predetermined amount V of liquid, the control unit 24 causes the valve 23 to open, so that the waste liquid flows into the collecting container 17. As soon as the second volumetric meter 22 has measured a predetermined amount v of liquid, the control unit 24 causes the valve 23 to close. And so on, until the end of the treatment session.

Figure 2:
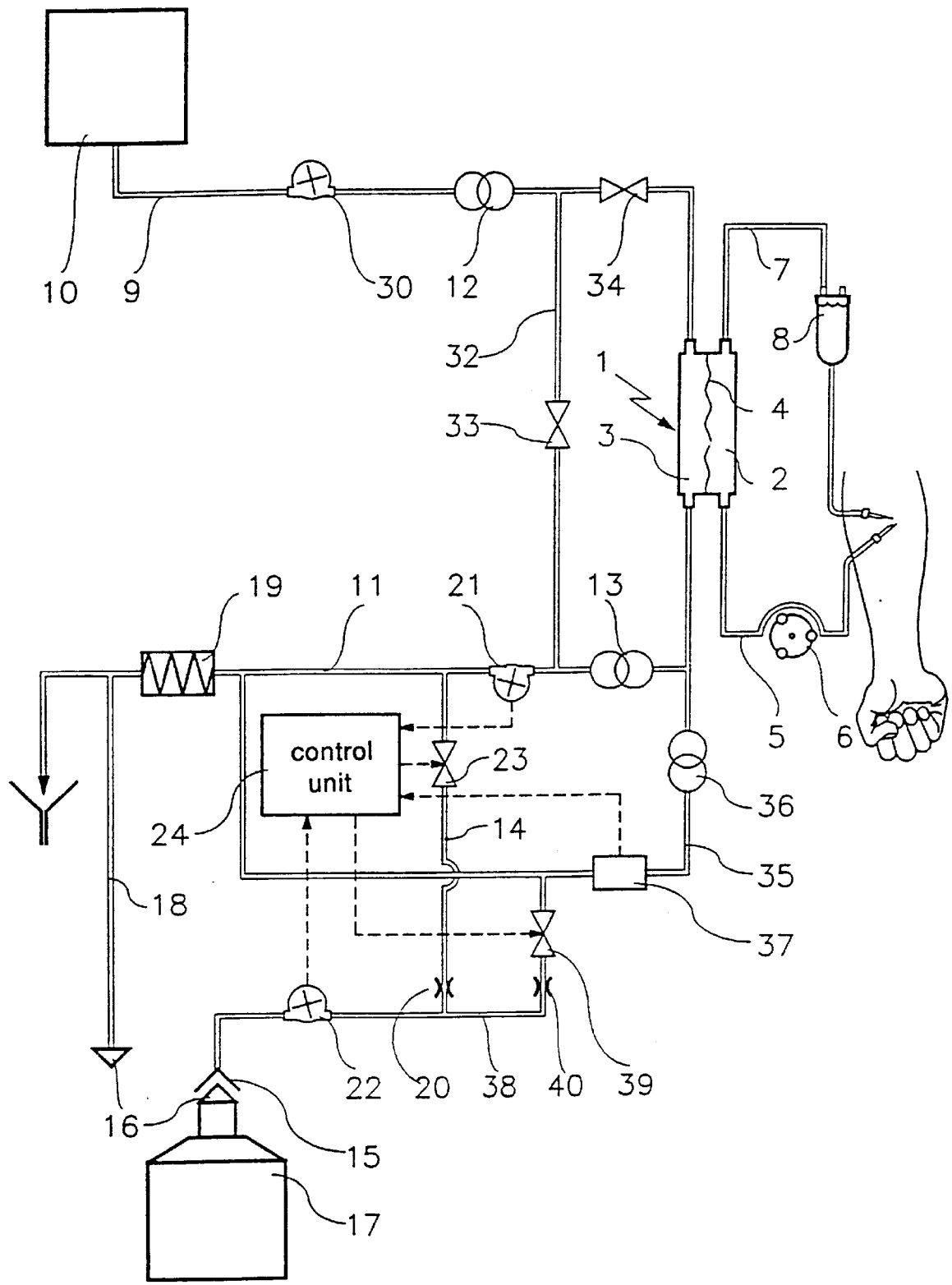
FIG. 2 is a simplified diagram of an apparatus for treatment of blood by extracorporeal circulation in accordance with a second embodiment of the invention.

The treatment apparatus represented in FIG. 2 differs from that which is represented in FIG. 1 in that it comprises a device for measuring the ultrafiltration flow rate in the exchanger requiring the circulation, at regular time intervals, of fresh dialysis liquid in the waste liquid line. The waste liquid sample collecting device of this apparatus is adjusted in order to take account of this restriction. It is also designed for operation of the device in haemofiltration mode, during which the only liquid which circulates in the dialysis liquid circuit is ultrafiltrate.

The identical or similar components of the devices of FIGS. 1 and 2 are identified by the same numerals.

The device for adjusting the ultrafiltration flow rate of this treatment apparatus comprises a first flowmeter 30 arranged on the feed line 9 upstream of the first circulation pump 12 and a second flowmeter 21 arranged on the discharge line 11 downstream of the second circulation pump 13. The pump 13 is subject to the comparison of the flow rates measured by the two flowmeters 30, 21, so that these flow rates are the same. The flowmeters 30, 21 are placed directly in series at regular time intervals for a calibration phase: to this end, the calibration line 32 is installed as a bypass of the exchanger 1 between a junction point with the feedline 9 situated downstream of the first circulation pump 12 and a junction point with the discharge line 11 situated downstream of the second circulation pump 13. The calibration line 32 is equipped with a valve 33 and the feed line 9 is equipped with a valve 34, the calibration line 32 being brought in line and off line under the control of the opening of a valve and the closing of another valve and vice versa.

A secondary discharge line 35 is connected, as a bypass of the discharge line 11, between a point situated upstream of the second circulation pump 13 and a point situated upstream of a temperature exchanger 19 arranged close to the free end of the discharge line 11. An extraction pump 36 and a third device 37 for measuring an amount of liquid, such as that which is described, for example, in European Patent No. 0,401,139, are arranged in series on this secondary discharge line. As the amounts of liquid circulating in the flowmeters 30, 21 are kept the same, the volume of waste liquid pumped by the extraction pump 36 out of the dialysis liquid circuit and delivered to the drain corresponds exactly to the volume of plasma water passing, by ultrafiltration, through the membrane 4 of the exchanger 1.

In addition to the components which have been described above with respect to FIG. 1, the sample collecting device of the apparatus represented in FIG. 2 comprises a second waste liquid withdrawal line 38 having an end connected to the secondary discharge line 35 downstream of the third means 37 for measuring an amount of liquid and another end which can be connected to the collecting container 17. Obturation means, such as a valve 39, a constriction element 40 and fourth means 22 for measuring an amount of liquid, such as a flowmeter, are arranged on this second withdrawal line 38. Advantageously, as represented in FIG. 2, the second and fourth means for measuring an amount of liquid are coincident (flowmeter 22) and are arranged on a portion of line common to the two withdrawal lines 38, 14.

The treatment apparatus which has just teen described operates in the following way:

During a treatment by dialysis (which generally always includes the ultrafiltration necessary to cause the patient to lose his excess weight), as well as during a treatment by haemodiafiltration, the valve 34 is opened, the valve 33 is closed, the two pumps 12 and 13 turn, the pump 12 at a stationary speed and the pump 13 at a variable speed adjusted so that the liquid inlet and outlet flow rates at the two flowmeters 30, 21 are the same. The extraction pump 36, the flow rate of which is adjusted by means of the device for measuring an amount of liquid 37, turns in order to extract from the dialysis circuit an amount of liquid corresponding to a desired amount of ultrafiltrate.

The control unit calculates successive volumes of liquid V=V1+V2 equal to the sum of volumes V1 measured by means of the flowmeter 21 and of volumes V2 measured by means of the measurement device 37. Each time that an amount of waste liquid V=V1+V2 has flowed in the discharge lines 11 and 35, the control unit 24 causes the valve 23 to open and consequently liquid to flow into the collecting container 17. Each time that an amount of liquid v, calculated by the control unit 24 from the data supplied by the flowmeter 22 situated on the withdrawal line 14, has flowed through this flowmeter, the control unit 24 causes the valve 23 to close.

During the dialysis session, the upstream and downstream flowmeters 30, 21 are regularly calibrated. The valve 34 is then closed, the valve 33 is opened and the pump 13 is stopped. The liquid which circulates in the discharge line 11 is fresh dialysis liquid. To avoid sampling the fresh dialysis liquid, which serves no practical purpose, the valve 23 remains closed between the time when the valves 33, 34 are positioned to enable the flowmeters to be calibrated and the time when their positions are reversed in order to re-establish the circulation of dialysis liquid in the exchanger 1.

In ultrafiltration mode, only the ultrafiltration pump 36 and the blood pump 6 operate. All the waste liquid flows via the secondary discharge line 35. Each time that an amount V' of liquid has been measured by the measurement element 37, the control unit 24 causes the valve 39 to open and each time that an amount v' of liquid, calculated by the control unit 24 from the data supplied by the flowmeter 22, has flowed through this flowmeter, the control unit causes the valve 39 to close.

The ratios V/v and V'/v' are the same.

The invention is not limited to the embodiments which have just been described and it is capable of alternative forms. In particular, it is possible to replace the constriction elements 19, 20, by virtue of which the ratio of the total waste liquid flow rate to the flow rate of the liquid sampled is substantially constant, by a pressure regulator, arranged downstream of the junction of the discharge line 11 with the withdrawal line 14, by virtue of which the flow rate of liquid sampled would be substantially constant.

What is claimed is:

1. A blood treatment circuit containing a blood treatment apparatus, the circuit comprising:
    a feedline for supplying fresh treatment liquid to the blood treatment apparatus;
    a waste liquid discharge line for evacuating waste liquid from the blood treatment apparatus;
    first measurement means for measuring an amount of liquid flowing through the waste liquid discharge line and for generating a signal indicative of a measured amount;
    a collecting container and an associated waste liquid withdrawal line for collecting a sample from the waste liquid discharge line, the withdrawal line having a first end connected to the waste liquid discharge line and a second end connected to the collecting container; and
    means for causing a metered flow of waste liquid into the collecting container at periodic intervals and as a function of volumetric flow through the waste liquid discharge line, to thereby collect a sample representative of all waste liquid discharged during at least a substantial portion of a treatment session, the metered flow causing means including second measurement means for measuring an amount of liquid flowing through the withdrawal line, obturation means for selectively restricting flow through the withdrawal line, and control means for selectively opening the obturation means each time the first measurement means has measured a predetermined volume $V_a$ and for closing the obturation means each time the second measurement means has measured a second predetermined volume $V_b$.

2. A device according to claim 1, further comprising means, connected to the waste liquid discharge line, for adjusting a flow rate in the waste liquid withdrawal line.

3. A device according to claim 2, wherein the means for adjusting the flow rate in the waste liquid withdrawal line includes a first liquid flow restriction element arranged on the withdrawal line and a second liquid flow restriction element arranged on the waste liquid discharge line downstream of a junction with the withdrawal line, so that the flow rate in the withdrawal line is substantially the same as a predetermined fraction of the flow rate in the discharge line.

4. A device according to claim 2, wherein the means for adjusting the flow rate in the waste liquid withdrawal line comprises a pressure regulator arranged on the waste liquid discharge line downstream of a junction with the withdrawal line, so that the flow rate in the withdrawal line is substantially constant.

5. A device according to claim 1, wherein the first measurement means includes a volumetric meter.

6. A device according to claim 1, wherein the second measurement means includes a volumetric meter.

7. A device according to claim 1, wherein the obturation means includes a valve arranged in one of the waste discharge line and the waste liquid withdrawal line.

8. A device according to claim 1, wherein the control means is additionally configured to control the obturation means to restrict liquid flow in the waste liquid withdrawal line and thereby enable a calibration phase wherein fresh treatment liquid is circulated in at least a portion of the waste liquid discharge line.

9. A blood treatment circuit containing a blood treatment apparatus, the circuit comprising:
    a feedline for supplying fresh treatment liquid to the blood treatment apparatus;
    a main waste liquid discharge line connectable to an outlet of the blood treatment apparatus;
    a secondary waste liquid discharge line, connected to the main waste liquid discharge line, and having an extraction pump therein;
    first measurement means in the main waste liquid discharge line for measuring an amount of liquid flowing through the main waste liquid discharge line and for supplying corresponding data;
    second measurement means in the secondary waste liquid discharge line for measuring an amount of liquid flowing through the secondary waste liquid discharge line and for supplying corresponding data; and
    a waste liquid collecting device including:
        a main waste liquid withdrawal line having a first end connectable to the main waste liquid discharge line downstream of the first measurement means, and a second end connectable to a collecting container;
        a secondary waste liquid withdrawal line having a first end connectable to the secondary waste liquid discharge line, downstream of the second measurement means, and a second end connectable to the collecting container; and
        means for causing a metered flow of waste liquid into the collecting container through the main waste liquid withdrawal line as a function of the data supplied by the first and second measurement means to thereby collect a sample representative of all waste liquid discharged throughout at least a substantial portion of a treatment session.

10. A device according to claim 9, wherein the means for causing is additionally configured to control, during calibration phases, obturation of the waste liquid withdrawal line.

11. A device according to claim 9, wherein the means for causing a metered flow of waste liquid into the collecting container includes:
    third measurement means arranged on the main waste liquid withdrawal line, for measuring an amount of liquid flowing therethrough, first obturation means arranged on the main waste liquid withdrawal line, and control means for opening the first obturation means each time the first measurement means has measured a first predetermined amount $V_a$ of waste liquid and for closing the first obturation means each time that the second measurement means has measured a second predetermined amount $V_b$ of waste liquid.

12. A device according to claim 11, wherein the means for causing a metered flow of waste liquid includes fourth measurement means, arranged on the secondary waste liquid withdrawal line, for measuring an amount of liquid flowing therethrough, second obturation means arranged on the secondary waste liquid withdrawal line, control means for controlling the opening of the second obturation means each time the second measurement means has measured a first predetermined amount V' of waste liquid and for closing the second obturation means each time the fourth measurement means has measured a second predetermined amount v' of waste liquid.

13. A device according to claim 12, wherein the third measurement means and the fourth measurement means are coincident and are arranged on a portion of line common to the main and secondary waste liquid withdrawal lines.

14. A device according to claim 9, further including means, connected to the main discharge line, for adjusting a flow rate in the main waste liquid withdrawal line.

15. A device according to claim 14, wherein the means for adjusting a flow rate in the main waste liquid withdrawal line includes a first liquid flow restriction element arranged on the main waste liquid withdrawal line and a second liquid flow restriction element arranged on the main waste liquid discharge line downstream of a junction of the main waste liquid discharge line with the main waste liquid withdrawal line, so that the flow rate in the main liquid withdrawal line is substantially the same as a predetermined fraction of the flow rate in the main waste liquid discharge line.

16. A device according to claim 14, wherein the means for adjusting the flow rate in the main waste liquid withdrawal line comprises a pressure regulator arranged on the main waste liquid discharge line downstream of a junction of the main waste liquid discharge line with the main waste liquid withdrawal line, so that the flow rate in the main waste liquid withdrawal line is substantially constant.

17. A device according to claim 9, wherein the first measurement means comprises a volumetric meter.

18. A device according to claim 9, wherein the second measurement means comprises a volumetric meter.

19. A device according to claim 9, wherein at least one of the first and second obturation means comprises a valve.

20. A blood treatment circuit connectable to a blood treatment apparatus, the circuit comprising:

a feedline for connectable to an inlet of the blood treatment apparatus for supplying fresh treatment liquid thereto;

a main waste liquid discharge line connectable to an outlet of the blood treatment apparatus;

a secondary waste liquid discharge line, connected to the main waste liquid discharge line, and having an extraction pumps therein;

first measurement means in the main waste liquid discharge line for measuring an amount of liquid flowing through the main waste liquid discharge line and for supplying corresponding data;

second measurement means in the secondary waste liquid discharge line for measuring an amount of liquid flowing through the secondary waste liquid discharge line and for supplying corresponding data; and a waste liquid collecting device including:

a main waste liquid withdrawal line having a first end connectable to the main waste liquid discharge line downstream of the first measurement means, and a second end connectable to a collecting container;

a secondary waste liquid withdrawal line having a first end connectable to the secondary waste liquid discharge line, downstream of the second measurement means, and a second end connectable to the collecting container;

third measurement means in the main waste liquid withdrawal line for measuring an amount of liquid flowing therethrough;

fourth measurement means in the secondary waste liquid withdrawal line for measuring an amount of liquid therethrough;

first obturation means arranged in the main waste liquid withdrawal line;

second obturation means arranged in the secondary waste liquid withdrawal line; and control means for opening the first obturation means each time the first measurement means has measured a first predetermined amount V of waste liquid and for closing the first obturation means each time the third measurement means has measured a second predetermined amount v of waste liquid, and for opening the second obturation means each time that the second measurement means has measured a first predetermined amount V' of waste liquid, and for closing the second obturation means each time that the fourth measurement means has measured a second predetermined amount v' of waste liquid.

* * * * *

UNITED STATES PATENT AND TRADEMARK OFFICE
CERTIFICATE OF CORRECTION

PATENT NO. : 5,954,951
DATED : September 21, 1999
INVENTOR(S) : Nuccio

It is certified that error appears in the above-identified patent and that said Letters Patent is hereby corrected as shown below:

Abstract, Front Page, line 13, change "predetermine" to --predetermined--.

Claim 20, Col. 9, line 29, after "feedline" delete "for"; and line 36, change "pumps" to --pump--.

Signed and Sealed this

Sixth Day of June, 2000

Attest:

Q. TODD DICKINSON

*Attesting Officer*      *Director of Patents and Trademarks*